United States Patent
Jiao et al.

(10) Patent No.: US 12,011,009 B2
(45) Date of Patent: Jun. 18, 2024

(54) MONASCUS PURPUREUS AND USE THEREOF

(71) Applicant: BRIGHT DAIRY & FOOD CO., LTD., Shanghai (CN)

(72) Inventors: Jingkai Jiao, Shanghai (CN); Zhenmin Liu, Shanghai (CN); Yuanrong Zheng, Shanghai (CN); Jing Liu, Shanghai (CN); Junwei Teng, Shanghai (CN)

(73) Assignee: BRIGHT DAIRY & FOOD CO., LTD., Shanghai (CN)

( * ) Notice: Subject to any disclaimer, the term of this patent is extended or adjusted under 35 U.S.C. 154(b) by 66 days.

(21) Appl. No.: 17/043,782

(22) PCT Filed: Mar. 10, 2020

(86) PCT No.: PCT/CN2020/078530
§ 371 (c)(1),
(2) Date: Sep. 30, 2020

(87) PCT Pub. No.: WO2021/134914
PCT Pub. Date: Jul. 8, 2021

(65) Prior Publication Data
US 2022/0183310 A1    Jun. 16, 2022

(51) Int. Cl.
*A23C 19/032*    (2006.01)
*A23C 19/06*    (2006.01)
*C12N 1/14*    (2006.01)

(52) U.S. Cl.
CPC ............ *A23C 19/032* (2013.01); *A23C 19/06* (2013.01); *C12N 1/145* (2021.05)

(58) Field of Classification Search
CPC ........ A23C 19/032; A23C 19/06; C12N 1/145
USPC .............................................. 426/34, 36, 37
See application file for complete search history.

(56) References Cited

U.S. PATENT DOCUMENTS

2021/0219564 A1*  7/2021  Wang ................. A23C 19/0325

FOREIGN PATENT DOCUMENTS

CN           104186683 A  *  8/2014

OTHER PUBLICATIONS

CN104186683A, Aug. 2014, translation.*

* cited by examiner

*Primary Examiner* — Changqing Li
(74) *Attorney, Agent, or Firm* — Rivka Friedman

(57) ABSTRACT

The present disclosure relates to the field of biotechnology, in particular, to a *Monascus purpureus* and use thereof. The present disclosure provides a *Monascus purpureus* under the accession number of CGMCC No. 18564. The cheese prepared by the *Monascus purpureus* provided by the present disclosure has good sensory parameters, low content of harmful substances and rich beneficial substances, and has good texture parameters and industrial prospect.

9 Claims, 2 Drawing Sheets
Specification includes a Sequence Listing.

MONASCUS PURPUREUS AND USE THEREOF

CROSS REFERENCES TO RELATED APPLICATIONS

This is a Sect. 371 National Stage application of a PCT International Application No. PCT/CN2020/078530, filed on Mar. 10, 2020, which claims priority of a Chinese Patent Applications No. 201911402946X, filed on Dec. 31, 2019, the content of which is hereby incorporated by reference in its entirety for all purposes.

TECHNICAL FIELD

The present disclosure relates to the field of biotechnology, in particular, to a *Monascus purpureus* and use thereof.

BACKGROUND

*Monascus* belongs to the *Monascus* family in the Ascomycetes class, and is widely used in fermented food, wine-making, and pharmacy in Asia. The earliest application of *Monascus* dates back to 800 BC. *Monascus* was commonly known as "Red Koji", "Red Vinasse", "ang-kak", "akakoji" and so on. *Monascus* can produce functional metabolites such as monacolin-K, red kojic acid DMA, isoflavones, γ-aminobutyric acid, etc., which are beneficial to the human body. *Monascus* is best known for being used as a food coloring agent as a traditional food popular in Asia, because *Monascus* can produce *Monascus* pigments, which are a group of *Monascus* natural metabolizing food pigments derived from polyketone chromophore β-keto acid. *Monascus* pigments are composed of red, orange, and yellow pigments with different chemical structures and similar properties. There are 10 known structures of *Monascus* pigment. *Monascus* pigments have better thermal stability than that of other synthetic pigments, and the heat resistance is excellent among natural pigments. *Monascus* pigments are not affected by common metal ions, oxidants and reducing agents, and have good coloring performance, strong bacteriostasis and antioxidant effects. *Monascus* pigments have been widely used in meat products, condiments, wine, pickled vegetables and flour products.

However, the application of *Monascus* is seriously limited due to the toxic substances of citrinin and bioamine produced by itself.

SUMMARY

The present disclosure provides a *Monascus purpureus* and use thereof, to solve the problems in the traditional technology.

The present disclosure provides a *Monascus purpureus* under the access number of CGMCC No. 18564.

Another aspect of the present disclosure provides the use of the *Monascus purpureus* in the preparation of dairy products.

In some embodiments of the present disclosure, the dairy product is selected from cheese, and the cheese is preferably selected from soft cheese, semi-soft cheese, or semi-hard cheese.

Another aspect of the present disclosure provides a method for preparing cheese, which is prepared from the *Monascus purpureus*.

In some embodiments of the present disclosure, the preparation method includes:
inoculating the *Monascus purpureus* in liquid milk containing a starter, fermenting and coagulating to provide curds;
draining the whey from the curds provided in step 1);
ripening the curds provided in step 2) in which the whey has been drained, to provide the cheese.

In some embodiments of the present disclosure, in the step 1), the liquid milk is pasteurized milk.

In some embodiments of the present disclosure, in the step 1), the *Monascus purpureus* is inoculated into liquid milk containing a starter.

Another aspect of the present disclosure provides a cheese prepared by the *Monascus purpureus* or by the method for preparing cheese.

In some embodiments of the present disclosure, the content of citrinin in the cheese is ≤200 ng/g, lovastatin ≥100 ng/g, and γ-aminobutyric acid ≥200 ng/g.

In some embodiments of the present disclosure, the hardness of the cheese is ≤500 g, the viscosity of the cheese is ≥25, and the elasticity of the cheese is ≥6.

DETAILED DESCRIPTION OF THE PREFERRED EMBODIMENTS

Figure 1:
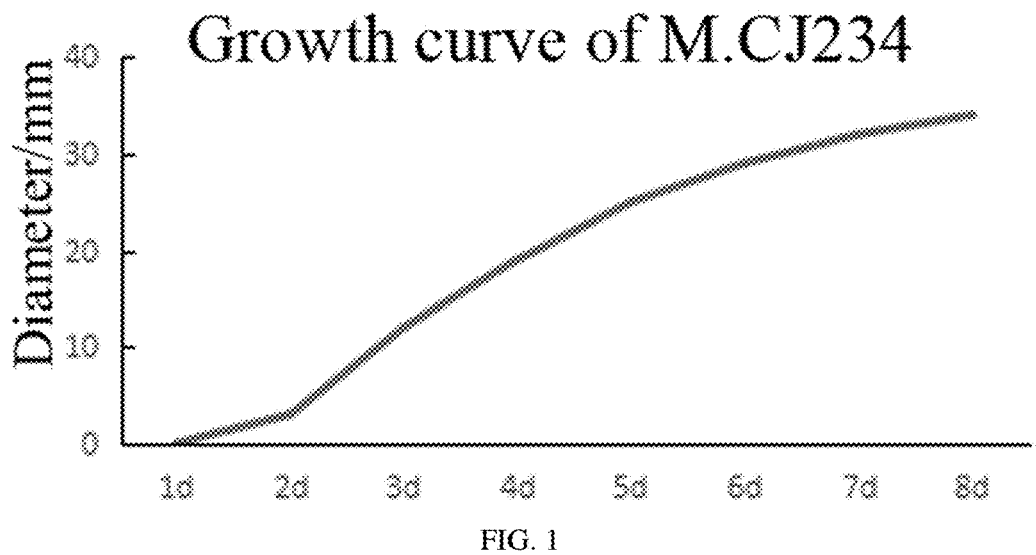
FIG. 1 is a schematic diagram showing the growth curve of the M.CJ234 in Embodiment 2 of the present disclosure.

To make the purpose, technical solution and beneficial technical effects of the present disclosure clear, embodiments will be described below for explaining the present disclosure in detail. Those skilled may easily understand other advantages and effects of the present disclosure according to contents disclosed by the specification.

Based on numerous practice and research, the inventor of the present disclosure accidentally isolated a strain of *Monascus purpureus* from *Monascus*-related products such as red koji rice, fermented bean curd, etc. The *Monascus purpureus* not only has an extremely high yield of *Monascus* pigment, but also can be applied to the fermentation of dairy products.

The first aspect of the present disclosure provides a *Monascus purpureus*, which is deposited in the China General Microbiological Culture Collection Center with the Accession No. CGMCC 18564. The ITS region (Accession: KY953214.1) of *Monascus purpureus* provided in the present disclosure has extremely high homology, and thus can be considered as Monascaceae in the Ascomycetes class.

The *Monascus purpureus* provided by the present disclosure can grow well in the medium. During the cultivation process, the linear growth of the growth curve increases with time. From day 2 to day 6 is the logarithmic phase of strain growth. From day 7, strain growth begins to slow down and enters a stable period, with good growth vigor. In addition, during the growth process, the *Monascus purpureus* can form *Monascus* pigment and secrete it into the medium to color the medium. The fermentation broth prepared by the *Monascus purpureus* has advantages in chromatic value and has a good color value. At the same time, the citrinin produced by *Monascus purpureus* is significantly less than other bacterial strains, while the amount of lovastatin, γ-aminobutyric acid and other substances produced is much higher than other bacterial strains.

The second aspect of the present disclosure provides the use of the *Monascus purpureus* provided in the first aspect of the present disclosure in the preparation of dairy products. The dairy product may be various dairy products that can be prepared by bacterial fermentation. For example, the dairy product may be cheese, and the cheese may be soft cheese, semi-soft cheese, and semi-hard cheese, or combinations thereof. For another example, cheese with MFFB (percentage of moisture after removing fat, i.e.: the mass of water in cheese/(mass of cheese-mass of fat in cheese)×100%) between 54-63 may be semi-hard cheese, and cheese with MFFB between 61-69 may be semi-soft cheese, and cheese with MFFB>67 may be soft cheese.

The third aspect of the present disclosure provides a method for preparing cheese, and the cheese is prepared from the *Monascus purpureus* provided in the first aspect of the present disclosure. A person skilled in the art may select a suitable method to obtain a cheese product by the *Monascus purpureus* provided in the first aspect of the present disclosure. For example, the method may include:
1) inoculating the *Monascus purpureus* provided in the first aspect of the present disclosure in liquid milk containing a starter, fermenting and coagulating to provide curds;
2) draining the whey from the curds provided in step 1), to provide the cheese.
3) ripening the curds provided in step 2) in which the whey has been drained, to provide the cheese.

In the preparation method provided by the present disclosure, the liquid milk is usually prepared from raw milk after being subjected to heat treatment. The raw milk usually refers to normal milk that is directly squeezed from the udders of healthy dairy animals without any change in composition, addition of foreign substances and processing. The raw milk usually meets the relevant standards in T/TDSTIA 001-2019, T/TDSTIA 002-2019 or T/TDSTIA 003-2019. The type of liquid milk usually corresponds to the type of raw milk. In a specific embodiment of the present disclosure, the raw milk may be raw cow milk or the like, and the liquid milk may be cow milk or the like. Generally speaking, the heat treatment process that raw milk is subjected to depends mainly on the treatment temperature (i.e., heating temperature) and treatment time of the process. Suitable heat treatment processes for raw milk should be known to those skilled in the art. For example, the liquid milk may be pasteurized milk. In the pasteurization, the treatment temperature may be 70-80° C., and the treatment time may be 15-20 s.

In the preparation method provided by the present disclosure, the *Monascus purpureus* is usually inoculated through seed medium. As described above, the *Monascus purpureus* provided by the first aspect of the present disclosure can grow well in the medium, so that the seed medium for the *Monascus purpureus* can be obtained conveniently. Those skilled in the art may select a suitable method to inoculate *Monascus* purpurea provided in the first aspect of the present disclosure into a medium, and cultivate under suitable conditions to provide a seed medium. For example, the applicable medium may be PDA (potato dextrose agar medium), wort agar medium and skimmed milk medium, etc. Preferably, the PDA includes 4-6 g/L potato powder and 18-22 g/L glucose, the pH value of the medium is 5.4-5.8. The skimmed milk medium may be a liquid medium or a solid medium, and the content of skimmed milk powder in the skimmed milk medium may be 10-14 wt. %. More preferably, the skimmed milk medium may be a solid skimmed milk medium. For another example, the culture temperature may generally be a temperature capable of growing the *Monascus purpureus*. Specifically, the culture temperature may be 15-45° C., 15-20° C., 20-23° C., 23-26° C., 26-29° C., 29-32° C., 32-35° C., 35-40° C., or 40-45° C., preferably, the culture temperature may be 26-35° C., and more preferably, the culture temperature may be 30-35° C. For another example, the culture can generally be performed under acidic conditions, and the preferred pH value may be 3.5-5.0, 3.5-4.0, 4.0-4.5, or 4.5-5.0. For another example, the culture time of each generation may be 5-9 days, 5-6 days, 6-7 days, 7-8 days, or 8-9 days. For another example, the inoculation volume may be 1-3v/v %. For another example, the number of activated generations for seed culture can be 2-3.

In the preparation method provided by the present disclosure, a person skilled in the art may select a suitable method to ferment and coagulate to provide curds. For example, the fermentation conditions in the step 1) may be medium-temperature fermentation, and the temperature conditions may specifically be between 30-36° C., 30-32° C., 32-34° C., or 34-36° C. For another example, the fermentation may last until the reaction system is weakly acidic. Specifically, the pH value of the reaction system may be 6.4-6.5. For another example, rennet can usually be added to the reaction system to coagulate the reaction system, and the concentration of the added rennet may be 0.04-0.2 g/10 L, 0.04-0.0.06 g/10 L, 0.06-0.08 g/10 L, 0.08-0.1 g/10 L, 0.1-0.15 g/10 L, or 0.15-0.2 g/10 L.

In the preparation method provided by the present disclosure, a person skilled in the art may select a suitable method to drain the whey from the curds to provide the cheese. For example, the curds may be stirred slowly to drain the whey from the curds.

In the preparation method provided by the present disclosure, a person skilled in the art may select a suitable method to ripen the curds in which the whey has been drained, to provide the cheese. For example, the curds in which the whey has been drained can be placed in the presence of salt. For another example, the culture temperature for ripening may be 8-15° C., 8-10° C., 10-13° C., or 13-15° C. For another example, the culture time for ripening may be 7-30 days, 7-10 days, 10-15 days, 15-20 days, 20-30 days, 30-60 days, 60-90 days, or longer.

The fourth aspect of the present disclosure provides a cheese, which is prepared by the *Monascus purpureus* provided in the first aspect of the present disclosure or by the method for preparing cheese provided in the third aspect of the present disclosure. The cheese prepared by the above preparation method has a compact texture and moderate elasticity. Covered with a layer of red skin, and the skin wrapped with a layer of white fluff, the cheese exudes characteristic cheese aroma and has a characteristic cheese flavor. In the cheese prepared by the above preparation method, the content of citrinin is far lower than domestic and international standards. The cheese is also rich in γ-aminobutyric acid and lovastatin. For example, the content of citrinin in the cheese may be ≤200 ng/g, ≤150 ng/g, ≤100 ng/g, ≤85 ng/g, ≤75 ng/g, or ≤70 ng/g, the content of γ-aminobutyric acid in the cheese may be ≥100 ng/g, ≥120 ng/g, ≥140 ng/g, ≥155 ng/g, ≥160 ng/g, ≥165 ng/g, or ≥170 ng/g, and the content of lovastatin in the cheese may be ≥200 ng/g, ≥250 ng/g, ≥300 ng/g, ≥350 ng/g, ≥400 ng/g, ≥420 ng/g, or ≥450 ng/g. In addition, the cheese prepared by the above preparation method also has good texture parameters. Compared with the cheese prepared by other bacterial strains under the same process conditions, the hardness of the cheese of the present disclosure has a significant decrease, while the viscosity and elasticity significantly increase. For example, the hardness of the cheese may be ≤500 g, ≤450 g, or ≤400 g, the viscosity of the cheese may be ≥25, ≥28, ≥30, ≥31, ≥32, or ≥33, and the elasticity of the cheese may be ≥6, ≥7, ≥8, or ≥9. The texture parameters can be measured by a texture analyzer.

The present disclosure provides a *Monascus purpureus* CGMCC No. 18564, and further provides the use thereof in the preparation of cheese. The cheese prepared by the *Monascus purpureus* has good sensory parameters, low content of harmful substances and rich beneficial substances, and has good texture parameters and industrial prospects.

The present disclosure is illustrated in more detail by the following embodiments, however, these embodiments are not limiting the scope of the present disclosure.

Unless otherwise stated, the experimental methods, detection methods, and preparation methods disclosed in the present invention all employ conventional techniques of molecular biology, biochemistry, chromatin structure and analysis, analytical chemistry, cell culture, recombinant DNA technology in the technical field and related fields. These techniques are well described in the existing literature. For details, see Sambrook et al. MOLECULAR CLONING: A LABORATORY MANUAL, Second edition, Cold Spring Harbor Laboratory Press, 1989 and Third edition, 2001; Ausubel et al, CURRENT PROTOCOLS IN MOLECULAR BIOLOGY, John Wiley & Sons, New York, 1987 and periodic updates; The series METHODS IN ENZYMOLOGY, Academic Press, San Diego; Wolfe, CHROMATIN STRUCTURE AND FUNCTION, Third Edition, Academic Press, San Diego, 1998; METHODS IN ENZYMOLOGY, Vol. 304, Chromatin (P. M. Wassarman and A. P. Wolfe, eds.), Academic Press, San Diego, 1999; and METHODS IN MOLECULAR BIOLOGY, Vol. 119, Chromatin Protocols (P. B. Becker, ed.) Humana Press, Totowa, 1999, and the like.

Embodiment 1

Acquisition of *Monascus* Purpureus CGMCC No. 18564

Red kojic rice samples were obtained from Lishui, Zhejiang, and the red kojic rice wine was brewed at 30° C. for 1-2 months. From the red kojic rice wine, the rice grains and rice juice were picked, and then streaked and plated on the PDA solid medium for separation and purification. The bacteria were screened according to the microbial characteristics and physiological characteristics to obtain the bacterial strain M.CJ234. The colony was pale pink at first, then matured into purple-red and covered with white fluff. Microscopic observation shows that the hypha is red and slender and curved, with few branches, with a transverse septum, containing air bubbles or oil droplets. The conidia are large in amount, red, and pear-shaped or globose. The ascospores are large in amount and ellipsoidal. Cleistothecia are occasionally observed, most of which are broken; the cleistothecia are ellipsoidal and contain many ascospores.

The *Monascus purpureus* M.CJ234 was deposited in China General Microbiological Culture Collection Center (CGMCC) in October 2019 with the Accession No. CGMCC 18564. The name of the culture is *Monascus purpureus*, and the classification name is *Monascus purpureus*.

Embodiment 2

Culture Characteristics of *Monascus Purpureus* CGMCC No. 18564

The growth curve of *Monascus purpureus* CGMCC No. 18564 was measured by straight-line growth rate. An appropriate amount of melted PDA agar medium was added to a U-shaped culture tube to reach half of the diameter of the culture tube. Sterilizing the U-shaped culture tube after adding cotton plugs at both ends, inoculating from one end after solidification, and then measuring the growth distance on time and calculating the growth rate. As shown in FIG. 1, the growth curve of *Monascus purpureus* CGMCC No. 18564 is lengthened with time. From day 2 to day 6 is the logarithmic phase of strain growth. From day 7, strain growth begins to slow down and enters a stable period.

a) Chromatic Value

*Monascus purpureus* CGMCC No. 18564 was inoculated into a triangular flask containing sterilized PDA medium with an inoculation volume of 1% (v/v). The triangular flask was placed in a 30° C. constant temperature incubator for culture. After 5-7 days of cultivation, the chromatic value was measured using a colorimeter. As shown in Table 1, the chromatic values of *Monascus purpureus* M.CJ234 (CGMCC No. 18564) and some other screened *Monascus* strains are listed. It can be found that the fermentation broth of *Monascus purpureus* M.CJ234 has certain advantages in the redness value a*.

TABLE 1

The chromatic value of the fermentation broth of the bacterial strain (the true value is between ±2%)

Figure 2:
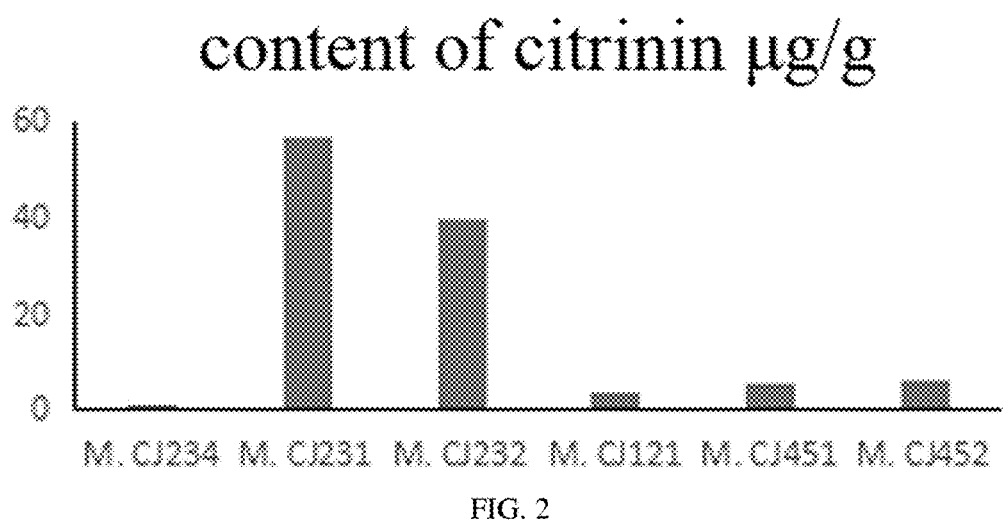
FIG. 2 is a schematic diagram showing the content of citrinin in the culture fermentation broth of each bacterial strain in Embodiment 2 of the present disclosure.
Figure 3:
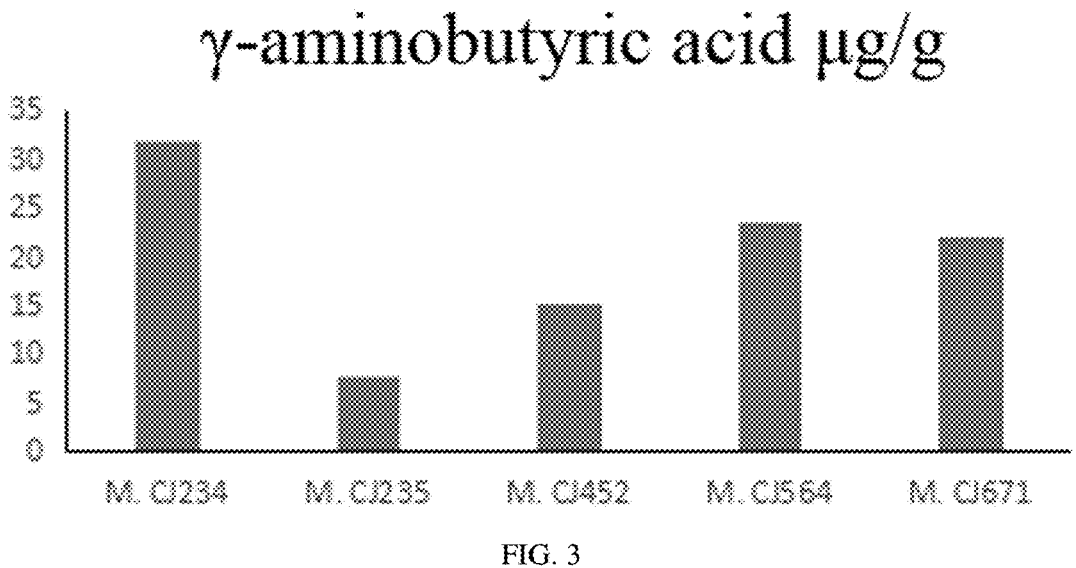
FIG. 3 is a schematic diagram showing the content of γ-aminobutyric acid in the culture fermentation broth of each bacterial strain in Embodiment 2 of the present disclosure.
Figure 4:
FIG. 4 is a schematic diagram showing the soft cheese prepared by the *Monascus purpureus* CGMCC No. 18564 according to Embodiment 4 of the present disclosure.

| Strain number | L* | a* | b* |
|---|---|---|---|
| M.CJ234 | 8.53 | 14.39 | 12.84 |
| M.CJ342 | 5.74 | 13.01 | 8.11 |
| M.CJ122 | 2.50 | 5.35 | 3.92 |
| M.CJ011 | 4.30 | 8.89 | 6.27 | b) Color value 0.5 g of 10-times diluted *Monascus purpureus* CGMCC No. 18564 culture (prepared in Embodiment 2, step a)) was added to 5 ml of 95 wt % ethanol water for extraction for 2 h, and then centrifuged at 6000 rpm for 15 min. The color values of the yellow pigment, orange pigment and red pigment of the supernatant were measured using a spectrophotometer at wavelengths of 400 nm, 470 nm and 500 nm, respectively. The color values of the three pigments of *Monascus purpureus* CGMCC No. 18564 are about 3.11, 2.07 and 2.39.

c) Biomass 10 g of *Monascus purpureus* CGMCC No. 18564 culture (prepared in Embodiment 2, step a)) was centrifuged (6000 g, 10 min, 4° C.). The cells were collected, washed three times with distilled water, dried in a 60° C. oven to constant weight, and then cooled in a desiccator. The biomass of *Monascus purpureus* CGMCC No. 18564 was measured to be about 5 g/L.

d) Citrinin 1 g of *Monascus purpureus* CGMCC No. 18564 culture (prepared in Embodiment 2, step a)) was added with 10 ml 75 wt % ethanol water and sonicated for 30 min, then centrifuged at 13000 rpm for 10 min. Membrane filtration was performed using Whatman filter No. 1, and then evaporated under vacuum at 55° C. 1 ml methanol was used to dissolve the residue, and 0.45 μm membrane was used for filtration. The content of citrinin in the fermentation broth of the medium was determined by HPLC. As shown in FIG. 2, the contents of citrinin in the fermentation broth of *Monascus purpureus* M.CJ234 (CGMCC No. 18564) and some *Monascus* strains are listed. It can be found that the amount of citrinin produced by M.CJ234 is significantly lower than that by other strains.

d) Lovastatin 1 g of *Monascus purpureus* CGMCC No. 18564 culture (prepared in Embodiment 2, step a)) was added with 5 ml 68 wt % ethanol water, leached at 200 rpm for 1 h, and placed in a 40° C. water bath for leaching for 12 h. The supernatant was centrifuged at 2000 g for 15 min. Membrane filtration was performed using Whatman filter No. 1, and then evaporated under vacuum at 55° C. 1 ml methanol was used to dissolve the residue, and 0.45 μm membrane was used for filtration. The content of lovastatin in the fermentation broth of the medium was determined by HPLC to be about 2.2 ng/g.

e) γ-aminobutyric Acid 1 g of *Monascus purpureus* CGMCC No. 18564 culture (prepared in Embodiment 2, step a)) was added with 6 ml 4 wt % acetic acid aqueous solution for leaching for 1 h, then centrifuged at 6037 g for 15 min. The supernatant was added with 4 ml ethanol and centrifuged again at 16770 g for 20 min. Then evaporated under vacuum. 0.5 ml of distilled water was added and 0.45 μm membrane was used for filtration. An amino acid analyzer was used for analysis. As shown in FIG. 3, the content of γ-aminobutyric acid was determined to be about 31.89 μg/g, which was significantly higher than that of γ-aminobutyric acid in the culture fermentation broth of other strains.

f) ITS Sequence Analysis

ITS sequence analysis: using primers to amplify the ITS region of *Monascus purpureus* CGMCC No. 18564, the forward primer sequence is shown in SEQ ID NO. 1, the reverse primer sequence is shown in SEQ ID NO. 2:

```
Forward primer:
                                           (SEQ ID NO. 1)
TCCGTAGGTGAACCTGCGG Reverse primer:
                                           (SEQ ID NO. 2)
TCCTCCGCTTATTGATATGC
```

The PCR amplification system is as follows:

| Reagent | volume |
|---|---|
| Genomic DNA (20 ng/ul) | 1.0 ul |
| 10 × Buffer (containing 2.5 mM Mg2+) | 5.0 ul |
| Taq polymerase (5 u/μL) | 1.0 ul |
| dNTP (10 mM) | 1.0 ul |
| Forward primer (10 uM) | 1.5 ul |
| Reverse primer (10 uM) | 1.5 ul |

The PCR amplification system is as follows:

| Pre-denaturation | Denaturation | Annealing | Extension | Final extension | PCR cycles |
|---|---|---|---|---|---|
| 95° C., 5 min | 95° C., 30 s | 58° C., 30 s | 72° C., 1 min | 72° C., 7 min | 35 |

After the reaction, 3 ul of PCR product was detected by 1% agarose gel electrophoresis to confirm the PCR amplified fragments. The PCR product was recovered with the AxyPrep DNA gel extraction kit, and then the DNA sequencing was performed using the sequencer AB13730-XL (Shanghai Personalbio Co., Ltd.). The sequencing results are shown in SEQ ID NO. 3. Comparing the spliced sequence files with the data in NCBI nucleic acid database by using Blast program, it was found that the homology between the PCR product and the *Monascus purpureus* was 99.63%. When the sequence homology is higher than 97%, it can be considered as the same specie within the genus. Therefore, M.CJ234/CGMCC No. 18564 is considered as *Monascus purpureus*.

```
                                           (SEQ ID NO. 3)
GATGGTACCTACCTGATCGAGGTCACCTAAGGAAAAAAGGTTGGAGAGGG

CAAAGGCCCCGGCCCGACCTACTGAGCGGGTGACAAAGCCCCATACGCTC

GAGGACCGGACGCGGCGCCGCCACTGCCTTTCGGGCCCGTCCCCGTTGCC

CGGAGGCGCAGGGGACGGCGGCCCAACACACAAGCCGCGCTTGAGGGGCA

GTAATGACGCTCGGACAGGCATGCCCCCCGGAATACCAGGGGGCGCAATG

TGCGTTCAAAGATTCGATGATTCACTGAATTCTGCAATTCACATTACTTA

TCGCATTTCGCTGCGTTCTTCATCGATGCCGGAACCAAGAGATCCGTTGT

TGAAAGTTTTAACCGATTTGGTATGTTTACTCAGACAGCAATCCTTTTCA

AAGACAGCGTTCGAGAAGATGTCTCCGGCGGGCCCCAGGGGGCCGCGCCG

AAGCAACAGGAGGTACAATAATCACGGGTGGGAGGTTGGGTCCCACGAAG

GGGACCCGCACTCGGTAATGATCCTTCCGCAGGTTCACCTACGGAAG
```

Embodiment 3

Preparation of Starter Containing *Monascus Purpureus* CGMCC No. 18564

Liquid seed medium: PDA medium is a conventional PDA medium in the field, consisting of potato powder 5 g/L, glucose 20 g/L, and with pH 5.6. *Monascus purpureus* M.CJ234 was inoculated into the above-mentioned medium (sterilized at 121☐ for 20 min) with an inoculation volume of 2% (v/v). The medium was placed in a 30° C. constant temperature incubator for culturing for 7 days and activated for 2 generations to obtain the starter 1.

Solid seed medium: skimmed milk powder (purchased from Westland Co-operative Dairy Co., Ltd., New Zealand) was dissolved in water to obtain the skimmed milk medium. The skimmed milk medium was sterilized at 115° C. for 15 min, and then mixed with sterilized agar to obtain a solid skimmed milk medium. In the solid skimmed milk medium, the proportion of skimmed milk powder is 12 wt %, and the proportion of agar is 0.2 wt %. *Monascus purpureus* M.CJ234 was streaked and inoculated into the above-mentioned medium. The medium was placed in a 30° C. constant temperature incubator for culturing for 7 days and activated for 2 generations to obtain the starter 2.

Embodiment 4

1) Filtering 50 L of raw cow's milk, stirring evenly, pasteurizing at 80-85° C. for 1 min, then cooling to 35° C. The obtained pasteurized milk was inoculated with commercial starter FD-DVS CHN-22 (Chr. Hansen Co., Ltd.), and the inoculation volume was 0.05 g/kg of liquid milk. The starter 1 obtained in Embodiment 3 was poured into the pasteurized liquid milk so that the concentration of the starter 1 in the liquid milk was 1v/v %. At a temperature after cooling (35° C.), fermenting to pH 6.5, adding 0.5 g/50 L rennet (Fromase 750XLG, purchased from Chr. Hansen Co., Ltd.), and curding for 30 min.

2) Cutting the curds prepared in step 1) into clots with a volume of 1.2 cm3 and slowly stirring for 30 min. Then draining all the whey. Adding the whay-drained curds into a round mold and placing at 18° C. for 15 h, inverting for 3 times during the process. Salting in saturated salt water for 3 h and drying at 18° C. for 6 h. Then culturing at 30° C. for 3 days and transferring to 12° C. for 30 days to obtain soft Monascus cheese.

Embodiment 5

1) Filtering 50 L of raw cow's milk, stirring evenly, pasteurizing at 80-85° C. for 1 min, then cooling to 35° C. The obtained pasteurized milk was inoculated with commercial starter CHOOZIT™ RM 32 (DANISCO Co., Ltd.), and the inoculation volume was 0.05 g/kg of liquid milk. The surface colony of the starter 3 prepared in Embodiment 3 was scraped into liquid milk, so that the inoculation concentration of the solid starter 3 in the liquid milk was 1 g of solid starter per 100 ml of liquid milk. At a temperature after cooling (35° C.), fermenting to pH 6.4, adding 0.4 g/50 L rennet (Fromase 750XLG, purchased from Chr. Hansen Co., Ltd.), and curding for 45 min.

2) Cutting the curds prepared in step 1) into clots with a volume of 1 cm3 and slowly stirring for 45 min. Then draining all the whey. Adding the whey-drained curds into a round mold and placing at 18° C. for 15 h, inverting for 3 times during the process. Salting in saturated salt water for 3 h and drying at 18° C. for 6 h. Then culturing at 32° C. for 3 days and transferring to 12° C. for 30 days to obtain semi-soft Monascus cheese.

Embodiment 6

1) Filtering 50 L of raw cow's milk, stirring evenly, pasteurizing at 75° C. for 3 min, then cooling to 32° C. The obtained pasteurized milk was inoculated with commercial starter FD-DVS CHN-22 (Chr. Hansen Co., Ltd.), and the inoculation volume was 0.05 g/kg of liquid milk. The starter 1 obtained in Embodiment 3 was poured into the pasteurized liquid milk so that the concentration of the starter 1 in the liquid milk was 1v/v %. Adding 0.3 g/50 L rennet (Fromase 750XLG, purchased from Chr. Hansen Co., Ltd.) at the same time as the starter was added, and culturing to pH 6.5 at a constant temperature of 32° C.

2) Cutting the curds prepared in step 1) into clots with a volume of 1.4 cm3 and slowly stirring for 20 min. Washing the clots with water at 35° C. and keeping stirring for 25 min. Then draining all the whey. Adding the whey-drained curds into a square mold, squeezing for 75 min, and acidifying for 1 h. Adding 2% salt for 4 days, and the percentage is the mass percentage. Culturing at 32° C. for 3 days and transferring to 12° C., maturing for 3 months to obtain semi-soft Monascus cheese.

Control Example 1

1) The Monascus purpureus CGMCC No. 18564 in the preparation method of liquid seed medium in Embodiment 3 was replaced with M.CJ342, and the liquid seed medium starter 3 was obtained. The other preparations were identical to those in Embodiment 3.

2) The starter 1 in Embodiment 4 was replaced with the starter 3 obtained in the step 1), and the remaining preparations are exactly the same as in Embodiment 4.

The soft Monascus cheese in Control Example 1 was obtained.

Control Example 2

1) The Monascus purpureus CGMCC No. 18564 in the preparation method of solid seed medium in Embodiment 3 was replaced with M.CJ121, and the solid seed medium starter 4 was obtained. The other preparations were identical to those in Embodiment 3.

2) The starter 2 in Embodiment 5 was replaced with the starter 4 obtained in the step 1), and the remaining preparation is exactly the same as in Embodiment 5.

The semi-soft Monascus cheese in Control Example 2 was obtained.

Embodiment 7

The content of citrinin, lovastatin, and γ-aminobutyric acid in the cheese prepared in Embodiments 4-6 was further detected. For the specific detection method, please refer to Embodiment 2.

The detection results of each sample are shown in Table 2:

TABLE 2

Citrinin, lovastatin, γ-aminobutyric acid in monascus cheese

| Embodiment | Citrinin ng/g | Lovastatin ng/g | γ-aminobutyric acid ng/g |
|---|---|---|---|
| Embodiment 4 | 71.45 ± 0.03 | 155.00 ± 12.67 | 474.51 ± 12.60 |
| Embodiment 5 | 80.55 ± 0.12 | 174.26 ± 21.01 | 439.15 ± 10.68 |
| Embodiment 6 | 67.83 ± 0.09 | 168.98 ± 9.43 | 421.06 ± 4.67 |
| Control Example 1 | 944.13 ± 11.14 | 162.49 ± 22.57 | 128.00 ± 3.68 |
| Control Example 2 | 401.78 ± 3.18 | 139.66 ± 9.67 | 327.89 ± 3.89 |

It can be seen from Table 2 that the citrinin content in the cheese provided by the present disclosure is much lower than that in the Control Examples, and much lower than 200 ng/g for the Japanese standard, which is the most stringent international standard for citrinin. Meanwhile, the cheese provided by the disclosure also has a significant advantage in the content of γ-aminobutyric acid.

Embodiment 8

Determination of Texture in Monascus Cheese

The texture properties of the cheeses prepared in Embodiments 4-6 and Control Examples 1-2 were measured by a texture analyzer (purchased from Stable Micro Systems, UK). The measuring method is pressing downward, the test speed is 5.00 mm/sec. The test time is 5 seconds. The probe type is P/0.5R probe, each group of samples was measured 5 times in parallel. The average value was obtained. The results are shown in Table 3:

TABLE 3

Texture parameters of Monascus cheese

| Embodiment | Hardness/g | viscosity | elasticity |
|---|---|---|---|
| Embodiment 4 | 377.77 ± 13.97 | 33.72 ± 1.20 | 9.29 ± 0.80 |
| Embodiment 5 | 413.68 ± 18.06 | 30.58 ± 2.47 | 8.41 ± 0.62 |
| Embodiment 6 | 466.52 ± 10.35 | 31.24 ± 1.92 | 7.79 ± 1.21 |
| Control Example 1 | 273.04 ± 23.53 | 25.27 ± 4.65 | 5.87 ± 0.92 |
| Control Example 2 | 495.09 ± 7.62 | 24.68 ± 1.44 | 6.28 ± 1.82 |

It can be seen from Table 3 that the cheeses provided by the present disclosure and Control Example 2 are both semi-soft cheeses. The hardness of the cheeses in Embodiments is significantly reduced, and the Embodiments are significantly superior in viscoelasticity.

Embodiment 9

Sensory Evaluation Experiment:

The sensory evaluation includes two main items, the first item is Taste and Smell, and the second item is Texture, each item accounts for 25 points, the total score is 50 points. There are four sub-items under Taste and Smell, which are overall evaluation (total score of 10 points), cheese characteristic taste and odor (total score of 9 points), sourness (total score of 3 points), bitterness (total score of 3 points). There are three sub-items under the Texture, which are the tissue state (total score of 10 points), hardness (total score of 10 points), and plasticity (total score of 5 points). The specific methods of sensory evaluation are shown in Table 5:

TABLE 4

Cheese sensory evaluation method

| Item | Content |
|---|---|
| Taste and smell (25 points) | Overall: 10 points (good), 7 points (fair), 5 points (poor), 1 point (bad); Cheese characteristic taste and odor: 9 points (strong), 5 points (normal), 3 points (mild), 1 point (none); Sourness: 3 points (moderate sourness), 1 point (excessive sourness), 0 points (abnormal sourness); Bitterness: 3 points (no), 0 points (yes). |
| Texture (25 points) | Tissue state: 10 points (delicate), 8 points (even), 6 points (rough), 4 points (loose and fragile), 2 points (ground granulated); Hardness: 10 points (moderate), 6 points (a bit hard or a bit soft), 4 points (too hard or too soft); Plasticity: 5 points (good), 3 (yes), 0 points (no). |

There are a total of 20 sensory evaluators, 10 of which are researchers engaged in dairy research and development, and the other 10 have no background in dairy research. All the relevant scores are average scores. The sensory evaluation results of the cheese prepared in Embodiment 6 are shown in Table 6:

TABLE 6

Cheese sensory evaluation results

| Item | Content | Embodiment 4 | Embodiment 5 | Embodiment 6 | Control Example 1 |
|---|---|---|---|---|---|
| Taste and smell (25 points) | Overall (10 points) | 8 | 9 | 8 | 7 |
| | Cheese characteristic taste and odor (9 points) | 9 | 9 | 8 | 7 |
| | Sourness (3 points) | 3 | 2 | 3 | 2 |
| | Bitterness (3 points) | 2 | 2 | 2 | 1 |
| | Total score | 22 | 22 | 21 | 17 |
| Texture (25 points) | Tissue state (10 points) | 9 | 9 | 8 | 7 |
| | Hardness (10 points) | 9 | 8 | 9 | 8 |
| | Plasticity (5 points) | 4 | 3 | 4 | 3 |
| | Total score | 22 | 20 | 21 | 18 |

It can be seen from Table 6 that the cheeses prepared by the present disclosure is significantly superior to the cheeses prepared in the Control Examples in terms of overall preference, cheese characteristic taste, and tissue state, indicating that *Monascus purpureus* CGMCC No. 18564 is suitable for *Monascus* cheese production.

In summary, the present disclosure effectively overcomes various shortcomings and has high industrial utilization value.

The above-mentioned embodiments are just used for exemplarily describing the principle and effects of the present disclosure instead of limiting the present disclosure. Modifications or variations of the above-described embodiments may be made by those skilled in the art without departing from the spirit and scope of the disclosure. Therefore, all equivalent modifications or changes made by those who have common knowledge in the art without departing from the spirit and technical concept disclosed by the present disclosure shall be still covered by the claims of the present disclosure.

The invention claimed is:

1. A method for preparing cheese, comprising the following steps:
   1) inoculating a *Monascus purpureus* deposited in the China General Microbiological Culture Collection Center under an accession number of CGMCC No. 18564 in liquid milk containing a starter, fermenting and coagulating to provide curds;
   2) draining whey from the curds provided in step 1);
   3) ripening the curds provided in step 2) in which the whey has been drained, to provide the cheese, wherein step 3) comprises culturing the curds provided in step 2); wherein
   the culturing of the curds provided in step 2) consists of culturing at 30-32° C. for 3 days and then culturing at 12° C., thereby allowing a layer of red rind to grow on surfaces of the curds and then a layer of white fluff to grow on surfaces of the red rind layer.

2. The method for preparing cheese according to claim 1, wherein in step 1), the liquid milk is pasteurized milk.

3. The method for preparing cheese according to claim 1, wherein in step 1), the inoculating the *Monascus purpureus* in the liquid milk containing the starter is through a seed medium.

4. A cheese, prepared by the method for preparing cheese according to claim 1, wherein the cheese is selected from soft cheese, semi-soft cheese, or semi-hard cheese, and a hardness of the cheese is ≤500 g, a viscosity of the cheese is ≥25 g·sec, and an elasticity of the cheese is ≥6% and wherein an inoculation concentration of a solid starter containing the *Monascus purpureus* in liquid milk was 1% (w/v) or an inoculation concentration of a liquid starter containing the *Monascus purpureus* in liquid milk was 1% (v/v).

5. The cheese according to claim 4, wherein a content of citrinin in the cheese is ≤200 ng/g, a content of lovastatin in the cheese is ≥100 ng/g, and a content of γ-aminobutyric acid in the cheese is ≥200 ng/g.

6. The method for preparing cheese according to claim 1, wherein step 3) comprises culturing the curds provided in step 2) at 30° C. for 3 days and culturing at 12° C. for 30 days to obtain soft cheese.

7. The method for preparing cheese according to claim 1, wherein step 3) comprises culturing the curds provided in step 2) at 32° C. for 3 days and culturing at 12° C. for 30 days to obtain semi-soft cheese.

8. The method for preparing cheese according to claim 1, wherein step 3) comprises culturing the curds provided in step 2) at 32° C. for 3 days and culturing at 12° C., maturing for 3 months to obtain semi-hard cheese.

9. The method for preparing cheese according to claim 1, wherein the culturing of the curds provided in step 2) consists of culturing at 30-32° C. for 3 days and then culturing at 12° C. for 30 days.

* * * * *

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: The forward primer sequence to amplify the ITS
      region of Monascus purpureus CGMCC No. 18564

<400> SEQUENCE: 1
tccgtaggtg aacctgcgg                                                 19

<210> SEQ ID NO 2
<211> LENGTH: 20
<212> TYPE: DNA
<213> ORGANISM: Artificial Sequence
<220> FEATURE:
<223> OTHER INFORMATION: The reverse primer sequence to amplify the ITS
      region of Monascus purpureus CGMCC No. 18564

<400> SEQUENCE: 2
tcctccgctt attgatatgc                                                20

<210> SEQ ID NO 3
<211> LENGTH: 547
<212> TYPE: DNA
<213> ORGANISM: Artificial Sequence
<220> FEATURE:
<223> OTHER INFORMATION: Sequencing results of ITS sequence analysis

<400> SEQUENCE: 3
gatggtacct acctgatcga ggtcacctaa ggaaaaaagg ttggagaggg caaaggcccc       60
ggcccgacct actgagcggg tgacaaagcc ccatacgctc gaggaccgga cgcggcgccg     120
ccactgcctt tcgggcccgt cccgttgcc cggaggcgca ggggacggcg gcccaacaca     180
caagccgcgc ttgaggggca gtaatgacgc tcggacaggc atgcccccg gaataccagg      240 gggcgcaatg tgcgttcaaa gattcgatga ttcactgaat tctgcaattc acattactta     300
tcgcatttcg ctgcgttctt catcgatgcc ggaaccaaga gatccgttgt tgaaagtttt     360
aaccgatttg gtatgtttac tcagacagca atccttttca aagacagcgt tcgagaagat    420
gtctccggcg ggccccaggg ggccgcgccg aagcaacagg aggtacaata atcacgggtg    480
ggaggttggg tcccacgaag gggacccgca ctcggtaatg atccttccgc aggttcacct    540
acggaag                                                               547
```